(12) United States Patent
Zambelli et al.

(10) Patent No.: US 12,616,654 B2
(45) Date of Patent: May 5, 2026

(54) STAINLESS STEEL CAN FOR PRESSURISED METERED DOSE INHALERS

(71) Applicant: CHIESI FARMACEUTICI S.P.A., Parma (IT)

(72) Inventors: Enrico Zambelli, Parma (IT); Sauro Bonelli, Parma (IT); Diego Copelli, Parma (IT); Massimiliano Dagli Alberi, Parma (IT); Francesca Usberti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 900 days.

(21) Appl. No.: 17/776,168

(22) PCT Filed: Dec. 2, 2019

(86) PCT No.: PCT/EP2019/083347
§ 371 (c)(1),
(2) Date: May 11, 2022

(87) PCT Pub. No.: WO2021/110239
PCT Pub. Date: Jun. 10, 2021

(65) Prior Publication Data
US 2022/0395454 A1 Dec. 15, 2022

(51) Int. Cl.
| | |
|---|---|
| *A61K 9/00* | (2006.01) |
| *A61K 31/136* | (2006.01) |
| *A61K 31/4015* | (2006.01) |
| *A61K 31/573* | (2006.01) |
| *A61K 47/02* | (2006.01) |
| *A61K 47/10* | (2017.01) |
| *A61M 15/00* | (2006.01) |

(52) U.S. Cl.
CPC ............ *A61K 9/008* (2013.01); *A61K 31/136* (2013.01); *A61K 31/4015* (2013.01); *A61K 31/573* (2013.01); *A61K 47/02* (2013.01); *A61K 47/10* (2013.01); *A61M 15/0001* (2014.02)

(58) Field of Classification Search
CPC .. A61K 9/008; A61K 31/4105; A61K 31/573; A61K 47/02; A61K 47/10; A61M 15/0001
See application file for complete search history.

(56) References Cited

U.S. PATENT DOCUMENTS

| | | | |
|---|---|---|---|
| 2006/0257324 A1* | 11/2006 | Lewis | A61K 9/008 424/45 |
| 2011/0132355 A1* | 6/2011 | Gerhart | A61K 31/4704 128/200.23 |
| 2011/0150782 A1 | 6/2011 | Bonelli et al. | |
| 2011/0150784 A1 | 6/2011 | Bonelli et al. | |
| 2014/0363384 A1 | 12/2014 | Bonelli et al. | |
| 2015/0328144 A1 | 11/2015 | Bonelli et al. | |
| 2017/0079949 A1 | 3/2017 | Bonelli et al. | |
| 2018/0028439 A1* | 2/2018 | Scuri | A61M 15/0021 |
| 2019/0046433 A1 | 2/2019 | Bonelli et al. | |

FOREIGN PATENT DOCUMENTS

| | | |
|---|---|---|
| JP | 2013-515696 A | 5/2013 |
| JP | 2019-528316 A | 10/2019 |
| JP | 2019-529432 A | 10/2019 |
| WO | WO 2011/076843 A2 | 6/2011 |
| WO | WO 2015/101575 A1 | 7/2015 |
| WO | WO 2015/101576 A1 | 7/2015 |
| WO | WO 2018/033598 A1 | 2/2018 |
| WO | WO 2018/051131 A1 | 3/2018 |

OTHER PUBLICATIONS

Russian Office Action issued Dec. 21, 2022 in Russian Patent Application No. 202291710/28 (submitting English translation only), citing reference 15 therein, 8 pages.
International Search Report issued Aug. 20, 2020 in PCT/EP2019/083347, filed on Dec. 2, 2019, 4 pages.
Written Opinion issued Aug. 20, 2020 in PCT/EP2019/083347, filed on Dec. 2, 2019, 8 pages.
English translation of Chilean Search Report issued Dec. 21, 2023 in Chilean Application 202201414, 2 pages.
English translation of Eurasian Office Action issued Sep. 21, 2023 in Eurasian Patent Application No. 202291710/28, 4 pages.
English translation of Japanese Office Action issued Sep. 26, 2023 in Japanese Patent Application No. 2022-532870, 6 pages.
Brazilian Office Action issued Oct. 16, 2023 in Brazilian Patent Application No. BR112022010188-0 (with English language translation), 5 pages.

* cited by examiner

*Primary Examiner* — Zohreh A Fay

(74) *Attorney, Agent, or Firm* — Morgan, Lewis & Bockius LLP

(57) ABSTRACT
The invention generally refers to a stainless steel can for use in a metered dose inhaler device, containing an aerosol formulation, comprising glycopyrronium bromide and formoterol, or a salt or a solvate thereof, optionally in combination with one or more additional active ingredient, endowed with a high stability.

23 Claims, No Drawings

STAINLESS STEEL CAN FOR PRESSURISED METERED DOSE INHALERS

FIELD OF THE INVENTION

The present invention relates to an aerosol solution formulation intended for use with a pressurised metered dose inhaler (pMDI), comprising glycopyrronium bromide and formoterol, or a salt thereof or a solvate of said salt, optionally in combination with an inhalation corticosteroid (ICS), stabilised by a selected amount of a mineral acid, the said formulation being contained in a can made of stainless steel.

The invention further relates to the use of such pressurised metered dose inhaler comprising said formulation in a stainless steel can, in the prevention and therapy of airway diseases.

BACKGROUND OF THE INVENTION

Glycopyrronium bromide (also known as glycopyrrolate) is a muscarinic M3 anticholinergic agent used to reduce salivation associated with administration of certain anaesthetics, and as adjunctive therapy for peptic ulcers. It has also been reported to be effective in the treatment of asthmatic symptoms (Hansel et al., Chest 2005; 128:1974-1979).

WO 2005/107873 relates to the use of glycopyrrolate for the treatment of childhood asthma.

WO 01/76575 discloses a controlled release formulation for pulmonary delivery of glycopyrrolate, intended for use in the treatment of respiratory diseases, in particular of chronic obstructive pulmonary disease (COPD). WO 01/76575 focuses, essentially, on dry powder formulations suitable for delivery by means of a dry powder inhaler (DPI).

WO 2005/074918 discloses combinations of glycopyrrolate with glucocorticoid drugs and their use for treating diseases of the respiratory tract.

WO 2005/110402 refers to combinations of glycopyrrolate with a beta-2 agonist of the class of indane or of benzothiazole-2-one derivatives for the treatment of inflammatory or of obstructive airway diseases.

WO 2006/105401 refers to combinations of an anticholinergic, a corticosteroid and a long-acting beta-2 agonist for the prevention and treatment of respiratory, inflammatory or obstructive airway diseases; glycopyrrolate is among the optional anticholinergic agents.

According to WO 2007/057223 and WO 2007/057222, combinations of glycopyrronium bromide with an anti-inflammatory steroid, particularly mometasone furoate, are reported to provide a therapeutic benefit in the treatment of inflammatory and obstructive airways diseases.

WO 2007/057221 and WO 2007/057219 respectively refer to combinations of a glycopyrronium salt with an indanyl derivative beta-2 agonist (or analogue) or with an anti-inflammatory steroid, particularly mometasone furoate.

WO 00/07567 discloses, in example 4, a suspension aerosol formulation wherein to a mixture of micronized actives, namely formoterol fumarate, glycopyrronium bromide and disodium cromoglycate, a propellant mixture of HFA and dinitrogen monoxide, together with 2% by weight of ethanol, are added.

The "Martindale. The complete drug reference", January 2002, monograph on glycopyrronium bromide (page 467) shows that in investigations on compatibility of this substance with aqueous infusion solutions for injections and additives, the stability of glycopyrronium bromide is questionable above a pH 6, owing to ester hydrolysis.

US 2002/025299 discloses pressurised aerosol solution formulations of different active ingredients among which is formoterol or its combinations with a steroid such as beclometasone dipropionate, or with an anticholinergic atropine-like derivative such as ipratropium bromide, oxitropium bromide, tiotropium bromide, further acidified by HCl and stored in given cans such as stainless steel or anodised aluminium, or even lined with an inert organic coating.

WO 2005/074900 discloses an inhalable combination of an anticholinergic agent with a beta-2 mimetic agent for the treatment of inflammatory or obstructive respiratory diseases, the examples show formulations of the (R, R)-enantiomer of glycopyrronium bromide in combination with formoterol, either as DPI formulation or pMDI suspension.

US 2006/0257324 discloses the delivery of a combination of two or more dissolved drugs in a HFA propellant-cosolvent system, substantially having the same particle size distribution and thus allowing for their co-deposition in the same lung region. The therein described formulations comprise a beta-2 agonist (formoterol or carmoterol being exemplified) and a corticosteroid (beclometasone dipropionate being exemplified), or an anticholinegic agent such as ipratropium, oxitropium, tiotropium or glycopyrronium bromide, these latter being only generically cited in the description.

Formoterol is a beta-2 adrenergic agonist drug capable of relaxing smooth muscle in the bronchi and opening the airways to reduce wheezing conditions. It is commonly used as formoterol fumarate in the management of asthma and other respiratory conditions. It is known that aerosol solutions of formoterol fumarate are relatively unstable and have a short shelf-life when stored under suboptimal conditions.

In WO 2011/076843 the applicant further disclosed pMDI aerosol solution formulations comprising glycopyrronium bromide in combination with formoterol or salts thereof, optionally including an inhalation corticosteroid such as BDP or budesonide, wherein a suitable amount of a mineral acid was added, to achieve a proper stabilization of the final formulation. In addition, the above formulations enabled to maintain the amount of a degradation product, therein referred to as DP3, to low levels.

It has been noted that when using relatively high amounts of acid as a stabilizing adjuvant to both formoterol and glycopyrronium components, the amount of DP3 may increase to higher levels, as e.g. measurable upon storage for 3 months at 25° C., 60% of relative humidity.

Therefore, as e.g. disclosed in WO 2011/076843, a further step comprising removal of oxygen from the aerosol canister headspace, for instance by incorporating an oxygen purging step through vacuum crimping in the process of filling the aerosol canister, may be useful to control the DP3 content.

During the formulation development, the degradation product DP3 was identified as being N-(3-bromo)-[2-hydroxy-5-[1-hydroxy-2-[1-(4-methoxyphenyl)propan-2-ylamino]ethyl]phenyl]formamide (see analytical details in the experimental section).

As the formation of this DP3 degradation product, when it is quantified significantly above the identification/qualification threshold (≥1.0% w/w with respect to the theoretical formoterol fumarate content of 6 µg/actuation [as defined in ICH Guideline Q3B(R2)]) may represent a potential issue for these pMDI combination formulations, means for lowering DP3 content below an acceptable threshold, other than those known, involving oxygen removal and requiring a dedicated purging step in the filling of the aerosol canister during manufacturing, could be particularly advantageous.

As such, it would be thus desirable to provide a clinically useful aerosol combination product that combines the therapeutic benefits of formoterol or salts thereof or a solvate of said salt and glycopyrronium bromide, optionally in conjunction with additional active ingredients such as inhalation corticosteroids, in particular beclometasone dipropionate or budesonide, so that each individual pharmaceutically active component is properly delivered to the lungs in effective and consistent doses over an extended product lifetime, and ideally without the need for particular storage conditions of temperature or humidity, that could be otherwise required to maintain low levels of degradation products such as DP3.

In WO 2015/101576 and in WO 2015/101575 by the applicant, the amount of DP3 in HFA 134a-ethanol solution formulations comprising formoterol and glycopyrronium bromide has been kept under the limit of detection (i.e. of 0.10% w/w with respect to the theoretical formoterol fumarate content) when stored in accelerated conditions, at 25° C. and 60% relative humidity (RH), for at least 3 months respectively in aluminium cans internally coated by a resin comprising a fluorinated ethylene propylene (FEP) polymer or in cans provided with valves comprising at least a butyl rubber gasket.

We have now unexpectedly found that a proper storage in stainless steel aerosol cans of the above formulation of the combination comprising glycopyrronium bromide and formoterol, or a salt thereof or a solvate of said salt and optionally an ICS, in addition to minimize the amounts of degradation products during their shelf-life, particularly of DP3, even below the detection threshold as, for instance, determined after storage under severe conditions of temperature and humidity, could improve also the environmental sustainability of the product avoiding useless energy consumption, waste of resources and providing a more environmentally "clean" product.

Fluorocarbon polymers, commonly used to coat the interior can surfaces (to eliminate particle adhesion or deposition on can walls for suspension formulations or to improve chemical stability of solution formulations) are preferably selected from pure perfluoroalkoxyalkylene (PFA), polytetrafluoroethylene (PTFE), fluorinated ethylene propylene (FEP) polymers and blends such as for instance those with poly ether sulphone (PES).

The normally used coating techniques include spraying the inside of preformed cans, dipping or electrostatic dry powder coating, all followed by curing. Many of these processes require the use of solvents, which should then be removed, and the use of high temperatures (up to 400° C. when curing is required) and, in any case, a high energy consumption.

Therefore the use of a stainless steel can, avoids the additional steps of applying a polymeric coating to the metal aerosol can, involving transportations of goods from the can producer to a company specialised in the coating process (often a Contract Manufacturing Organisation (CMO)), and then to the manufacturer of the finished pressurised aerosol product. Moreover, a can made of stainless steel could be more easily recycled than a polymer coated aluminium can which, during its recycling and recovery by fusion, could develop, by combustion of the coating material, fumes and vapours potentially harmful to the air and the environment.

SUMMARY OF THE INVENTION

The present invention thus provides a pharmaceutical aerosol solution formulation intended for use in a pressurised metered dose inhaler comprising:

(a) glycopyrronium bromide at a dosage in the range of from about 5 µg to about 26 µg per actuation;

(b) formoterol, or a salt or a solvate therof, at a dosage in the range of from about 1 µg to about 25 µg per actuation;

(c) a HFA propellant;

(d) a co-solvent;

(e) a stabilising amount of a mineral acid; and optionally (f) an inhalation corticosteroid said formulation being contained in an aerosol can made in stainless steel.

According to the present invention, the amount of the degradation product N-(3-bromo)-[2-hydroxy-5-[1-hydroxy-2-[1-(4-methoxyphenyl)propan-2-ylamino]ethyl] phenyl]formamide, hereinafter shortly referred to as DP3, is lower than 0.10% w/w with respect to the theoretical formoterol fumarate content of 6 µg/actuation, which is the limit of quantification, when stored in accelerated conditions at 25° C. and 60% relative humidity (RH) for at least 3 months.

Optionally, the formulation further comprises an inhalation corticosteroid selected from the group consisting of beclometasone dipropionate, mometasone furoate, budesonide, flunisolide, fluticasone propionate, fluticasone furoate, ciclesonide, triamcinolone, triamcinolone acetonide, methylprednisolone and prednisone, where beclometasone dipropionate is particularly preferred.

In another aspect, the invention provides an aerosol can made of stainless steel containing a pharmaceutical solution formulation, said aerosol can being intended for use in a pressurised metered dose inhaler, wherein said solution comprises:

(a) glycopyrronium bromide, preferably at a dosage in the range of from about 5 µg to about 26 µg per actuation;

(b) formoterol, or a salt or a solvate thereof, preferably at a dosage in the range of from about 1 µg to about 25 µg per actuation;

(c) a HFA propellant;

(d) a co-solvent;

(e) a stabilising amount of a mineral acid; and, optionally, (f) an inhalation corticosteroid as above indicated, preferably beclometasone dipropionate.

In yet another aspect, the invention provides a method to lower the amount of degradation product N-(3-bromo)-[2-hydroxy-5-[1-hydroxy-2-[1-(4-methoxyphenyl) propan-2-ylamino]ethyl]phenyl]formamide (herein indicated as DP3) during the shelf-life of a pharmaceutical aerosol solution formulation intended for use in a pressurised metered dose inhaler comprising:

(a) glycopyrronium bromide, preferably at a dosage in the range of from about 5 µg to about 26 µg per actuation;

(b) formoterol, or a salt or a solvate thereof, preferably at a dosage in the range of from about 1 µg to about 25 µg per actuation;

(c) a HFA propellant;

(d) a co-solvent;

(e) a stabilising amount of a mineral acid; and, optionally, (f) an inhalation corticosteroid as above indicated, preferably beclometasone dipropionate, said method comprising containing the above formulation in a metal aerosol can made of stainless steel.

In yet another aspect, the invention provides a pressurised metered dose inhaler including an aerosol can made of stainless steel as a container for a pharmaceutical solution formulation comprising:

(a) glycopyrronium bromide, preferably at a dosage in the range of from about 5 µg to about 26 µg per actuation;

(b) formoterol, or a salt or a solvate thereof, preferably at a dosage in the range of from about 1 μg to about 25 μg per actuation;

(c) a HFA propellant;

(d) a co-solvent;

(e) a stabilising amount of a mineral acid; and, optionally, (f) an inhalation corticosteroid, as above indicated, preferably beclometasone dipropionate.

In yet another aspect, the invention provides an aerosol can made of stainless steel, as a container for a pharmaceutical solution formulation intended for use in a pressurised metered dose inhaler, said solution comprising:

(a) glycopyrronium bromide, preferably at a dosage in the range of from about 5 μg to about 26 μg per actuation;

(b) formoterol, or a salt or a solvate thereof, preferably at a dosage in the range of from about 1 μg to about 25 μg per actuation;

(c) a HFA propellant;

(d) a co-solvent;

(e) a stabilising amount of a mineral acid; and, optionally, (f) an inhalation corticosteroid, as above indicated, preferably beclometasone dipropionate.

In a further aspect the invention provides the use of an aerosol formulation as above described contained in a stainless steel can for the prevention and/or treatment of an obstructive respiratory disorder, including asthma and COPD.

DETAILED DESCRIPTION OF THE INVENTION

As above set forth, the present invention in one aspect refers to a pMDI formulation comprising formoterol fumarate, glycopirronium bromide and optionally a corticosteroid, that when stored in a stainless steel can shows an improved stability, as measurable e.g. by evaluating the amount of degradation products, particularly N-(3-bromo)-[2-hydroxy-5-[1-hydroxy-2-[1-(4-methoxyphenyl)propan-2-ylamino]ethyl]phenyl]formamide (herein indicated ad DP3). In this respect it is surprisingly found that when the herein detailed solution formulation comprising formoterol fumarate, glycopirronium bromide and optionally a corticosteroid, is stored in a can made of stainless steel, the amount of the DP3 degradation product is well below the limit of quantification. In other words, this means that the amount of DP3 detected when said solution formulation is stored in a stainless steel can according to the present invention is lower than 0.10% w/w with respect to the theoretical formoterol fumarate content of 6 μg/actuation, as herein below described in details.

In fact, it has been unexpectedly found that by the use of an aerosol can made of stainless steel, a pharmaceutical aerosol solution formulation as herein described in details shows a degradation profile which not only is useful for a proper use in the respiratory field, but it also shows a convenient stability over the time, even under severe conditions such as e.g. the storage at 25° C. and 60% relative humidity (RH) for at least 3 months. The containing and storage of the solution formulation as herein described in all the preferred embodiments, in a stainless steel according to the present invention, in fact, allows to maintain the level of the DP3 degradation product N-(3-bromo)-[2-hydroxy-5-[1-hydroxy-2-[1-(4-methoxyphenyl)propan-2-ylamino]ethyl]phenyl]formamide well below the 0.10% w/w, threshold limit with respect to the theoretical formoterol fumarate content (with 6 μg/actuation). It is recognized that said DP3 degradation product is generally formed by interaction of formoterol and glycopyrronium bromide, as detectable, for example, when the formulation is stored for prolonged period of time, or under accelerated conditions at 25° C. and 60% relative humidity (RH), for at least 3 months, independently from the metering valve type used.

Even further, it has now been surprisingly found that the pressurised aerosol solution formulation contained in a stainless steel can according to the present invention, when manufactured with a specific canister, after storage for at least 3 months at 25° C. and 60% RH, in addition to the degradation product DP3 level lower than the limit of quantification of 0.10% w/w (with respect to the theoretical formoterol fumarate content of 6 μg/actuation) showed an overall formoterol degradation products level within acceptable limits lower than 10% w/w (with respect to the theoretical formoterol fumarate content of 6 μg/actuation), preferably lower than 3% w/w and most preferably lower than 2% w/w.

Advantageously, it has also been found that, the maintenance of the residual level of formoterol fumarate, is higher than 90% w/w, preferably higher than 92% w/w and most preferably higher than 95% w/w with respect to its initial content, when the solution is contained in a stainless steel can according to the invention. Besides the above mentioned advantages, the use of a stainless steel can allows to maintain the glycopyrronium bromide and the optional inhalation corticosteroid levels at substantially the same as the respective initial levels.

Glycopyrronium bromide, chemically defined as 3-[(cyclopentylhydroxyphenylacetyl)oxy]-1,1-dimethylpyrrolidinium bromide, has two chiral centres corresponding to four potential different stereoisomers with configurations (3R,2'R)—, (3S,2'R)—, (3R,2'S)-and (3S,2'S)—. Glycopyrronium bromide, in the form of any of these pure enantiomers or diastereomers or any combination thereof, may be used in practising the present invention. In one preferred embodiment of the invention the racemic (threo) mixture constituted by (3S, 2'R)-and (3R, 2'S)-3-[(cyclopentylhydroxy phenylacetyl)oxy]-1,1-dimethylpyrrolidinium bromide, commonly used in therapy, also known as glycopyrrolate and hereinbelow defined as glycopyrronium bromide is used. The dosage of glycopyrronium bromide is comprised in the range from 5 to 26 μg per actuation, preferably from 6 to 25 μg per actuation, most preferably at 12.5 or 25 μg per actuation. Glycopyrronium bromide, in the formulation contained in a stainless steel can of the invention, is present in an amount preferably in the range from 0.004 to 0.12% w/w, preferably from 0.005 to 0.090% w/w, more preferably from 0.06 to 0.045% w/w, wherein % w/w means the amount by weight of the component, expressed as percent with respect to the total weight of the composition, when the cans are provided with valves delivering a volume of formulation in the range from 50 to 100 μl per actuation. The most preferred amount of glycopyrronium bromide is from 0.007 to 0.035% w/w when used with a valve delivering a volume of formulation of 63 μl per actuation.

Glycopyrronium bromide is commercially available, or it may be synthesized according to the process known in the art (see e.g. U.S. Pat. No. 2,956,062 or Franko BV and Lunsford CD, J Med Pharm Chem 2(5), 523-540, 1960).

Formoterol, normally used in therapy as the racemic mixture (R,R), (S,S) is chemically defined as (±), (R*, R*)—N-[2-hydroxy-5-[1-hydroxy-2-[1-(4-methoxyphenyl)propan-2-ylamino]ethyl]phenyl]formamide. Formoterol can be in the form of the free base, or as a salt or a solvate thereof. In one preferred embodiment of the invention formoterol is provided in the form of its fumarate salt and more preferably the solvate form of the formoterol salt is formoterol fumarate dihydrate. The dosage of formoterol fumarate dihydrate is comprised in the range from 1 to 24 µg per actuation, more preferably from 6 to 12 µg per actuation, being 6 µg or 12 µg particularly preferred. Formoterol fumarate dihydrate is present in the formulation contained in a stainless steel can of the invention in an amount in the range from 0.001 to 0.11% w/w, and preferably from 0.001 to 0.053% w/w when the cans are provided with valves delivering a volume of formulation in the range from 50 to 100 µl, the most preferred amount of formoterol fumarate dihydrate is from 0,001 to 0.032% w/w when used with a valve delivering a volume of formulation of 63 µl per actuation.

In one embodiment, the present invention refers to a formulation comprising formoterol, glycopyrronium bromide, a HFA propellant, a co-solvent, preferably ethanol, a mineral acid, preferably 1M HCl and an inhalation corticosteroid.

In this respect, a preferred inhalation corticosteroid is selected from the group of beclometasone dipropionate, budesonide or its 22R-epimer, ciclesonide, flunisolide, fluticasone propionate, fluticasone furoate, mometasone furoate, butixocort, triamcinolone acetonide, triamcinolone, methylprednisolone, prednisone, loteprednol and rofleponide. Preferably said inhalation corticosteroid is beclometasone dipropionate (BDP) or budesonide. In one more preferred embodiment, said inhalation corticosteroid is beclometasone dipropionate (BDP).

The inhalation corticosteroid is present at a dosage in the range from 20 to 1000 µg per actuation, preferably in the range from 50 to 250 µg per actuation. In preferred embodiments beclometasone dipropionate (BDP) is present at a dosage of 50, 100, 200 or 250 µg per actuation, more preferably of 100 or 200 µg per actuation. BDP is preferably present in the formulation contained in a stainless steel can of the invention in an amount from 0.04 to 1.1% w/w, more preferably from 0.066 to 0.556%, when the cans are provided with valves delivering a volume of formulation in the range from 50 to 100 µl, the most preferred amount of BDP is from 0.07 to 0.331% w/w when used with a valve delivering a volume of formulation of 63 µl per actuation.

It is preferred that the pharmaceutically active components of the formulation according to the invention are all dissolved in the mixture of propellant and co-solvent, in a substantially complete and homogeneous way. This means that the formulation of the invention is preferably a solution formulation.

As herein intended, "dissolved in a substantially complete and homogeneous way" means that the final formulation has a liquid form, substantially free of precipitates or insoluble residues.

Being the present invention preferably referred to a solution formulation wherein the active ingredients are completely dissolved in the formulation, when the description generically cites formoterol fumarate, both the forms of formoterol fumarate and formoterol fumarate dihydrate, which is its solvate form available in the market, are intended.

The co-solvent comprised into the formulations contained in a stainless steel can according to the present invention, is preferably characterized by having a higher polarity than the propellant and may include one or more substances such as a pharmaceutically acceptable alcohol and/or polyol, mainly intended to solubilize the pharmaceutically active components of the composition, preferably formoterol fumarate, glycopyrronium bromide and optionally an inhalation corticosteroid, in the selected propellant.

Preferably, the co-solvent is a lower branched or linear alkyl ($C_1$-$C_4$) alcohol, more preferably selected from isopropyl alcohol and ethanol, being ethanol even more preferred. In one particularly preferred embodiment, the co-solvent is anhydrous ethanol.

The polyol co-solvent when present is preferably selected from: glycerol, propylene glycol and polyethylene glycol.

The concentration of the co-solvent will generally vary depending e.g. on the final concentration of the active ingredients in the formulation or on the type of propellant. In one embodiment the co-solvent is anhydrous ethanol, preferably in a concentration suitable to completely dissolve the active ingredients in the formulation and comprised from 5 to 30% w/w, preferably from 7 to 25% w/w, more preferably from 10 to 15% w/w and most preferably 12% w/w.

The propellant component of the formulation contained in a stainless steel can according to the present invention, is a proper pressure-liquefied propellant, and it is preferably a hydrofluoroalkane (HFA) or a mixture of different HFAs. In one embodiment, the propellant is selected from the group consisting of HFA 134a (1,1,1,2-tetrafluoroethane), HFA 227 (1,1,1,2,3,3,3-heptafluoropropane), HFA 152a (1,1-difluoroethane) and mixtures thereof. In one preferred embodiment, the propellant is HFA 134a or HFA152a. HFAs may be present in the formulation in an amount in the range from 70 to 95% w/w, preferably from 80 to 93% w/w.

The mineral acid may be any pharmaceutically acceptable monoprotic or polyprotic acid, such as, but not limited to: hydrogen halides such as hydrochloric, hydrobromic, hydroiodic and hydrofluoric acid, phosphoric acid, nitric acid, sulphuric acid, and halogen oxoacids. The acid is generally present in an amount sufficient to stabilise glycopyrronium bromide and formoterol in a substantially complete and homogeneous way. In this respect, a preferred amount of mineral acid is an amount of acid equivalent to 1M hydrochloric acid (HCl) preferably in the range from 0.1 to 0.3 µg/µl of formulation, more preferably from 0.15 to 0.28 µg/µl, even more preferably from 0.18 to 0.26 µg/µl. These amount of 1M HCl present in the formulation contained in a stainless steel can of the invention correspond to amounts from 0.011 to 0.033% w/w, more preferably from 0.016 to 0.031% w/w, when the cans are provided with valves delivering a volume of formulation in the range from 50 to 100 µl, the most preferred amount of 1M HCl is from 0.017 to 0.029% w/w when used with a valve delivering a volume of formulation of 63 µl per actuation.

Preferably the mineral acid is 1M HCl, and different molarity than 1M or alternative inorganic acids may substitute for 1M HCl in the formulation of the invention. Optionally the aerosol solution formulation as intended in the present invention, may comprise other pharmaceutical excipients or additives known in the art. In particular, the formulation according to the invention may comprise one or more low volatility components. Low volatility components may be useful, for example, in order to increase the mass median aerodynamic diameter (MMAD) of the aerosol particles upon actuation of the inhaler and/or to improve the solubility of the active ingredient in the propellant/cosolvent mixture.

The low volatility component, when present, has preferably a vapour pressure at 25° C. lower than 0.1 kPa, even more preferably lower than 0.05 kPa. Examples of suitable low-volatility components are esters, preferably selected from isopropyl myristate, ascorbyl myristate, and tocopherol esters; glycols preferably selected from propylene glycol, polyethylene glycol and glycerol; and surface active agents preferably selected from saturated organic carboxylic acids, preferably lauric, myristic, stearic acid and unsaturated carboxylic acids, preferably oleic or ascorbic acid.

The amount of low volatility component may vary from 0.1 to 10% w/w, preferably from 0.5 to 5% w/w, more preferably between 1 and 2% w/w.

Desired doses of the individual pharmaceutically active components of the formulation are dependent on the identity of the component and the type and severity of the disease condition but are preferably such that a therapeutic amount of the active ingredient is delivered in one or two actuations. Generally, the doses of active ingredients are in the range of about 0.5-1000 μg per actuation, preferably about 1-300 μg/actuation, or about 5-150 μg/actuation.

The pharmaceutical formulation of the invention is contained in a stainless steel can, suitable for the use in a pMDI device known in the art.

According to the invention the aerosol cans are made of stainless steel. Preferred grade stainless steel suitable for pharmaceutical application is selected from: grade 904L, 316, 316L, 305, 304, 304L, 6Mo and 2205.

In a preferred embodiment the invention provides a pharmaceutical aerosol solution formulation intended for use in a pressurised metered dose inhaler comprising:

(a) glycopyrronium bromide at a dosage in the range from 5 to 26 μg per actuation, preferably from 6 to 25 μg per actuation, most preferably at 12.5 or 25 μg per actuation;

(b) formoterol, or a salt thereof or a solvate of said salt, at a dosage in the range from 1 to 24 μg per actuation, more preferably from 6 to 12 μg per actuation, being 6 μg or 12 μg particularly preferred;

(c) a HFA propellant in an amount in the range from 70 to 95% w/w, preferably from 80 to 93% w/w;

(d) a co-solvent consisting of ethanol in a concentration comprised from 5 to 30% w/w, preferably from 7 to 25% w/w, more preferably from 10 to 15% w/w and most preferably 12% w/w;

(e) a stabilising amount of a mineral acid; and, optionally (f) an inhalation corticosteroid selected from beclomethasone dipropionate at a dosage of 50, 100, 200 or 250 μg per actuation, preferably 100 or 200 μl wherein said formulation being contained in an aerosol can made in stainless steel.

The can is typically sealed with a metering valve for delivering a therapeutically effective dose of the active ingredients, according to methods known in the art. Generally, the metering valve assembly comprises a ferrule having an aperture formed therein, a body moulding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise an elastomeric material selected from EPDM (ethylene propylene diene monomer), neoprene and butyl rubber. Among the butyl rubbers chlorobutyl and bromobutyl rubber are preferably selected. EPDM rubber is particularly preferred.

The metering chamber, core and core extension are manufactured using suitable materials such as stainless steel, polyesters (e.g. polybutyleneterephthalate (PBT)), or acetals. The spring is manufactured in stainless steel eventually including titanium. The ferrule may be made of a metal, for example aluminium, aluminium alloy, stainless steel or anodized aluminium. suitable valves are available from manufacturers such as, for instance, Valois-Aptar, Bespak plc, V.A.R.I., 3M-Neotechnic Ltd, Rexam, Coster.

The pMDI is actuated by a metering valve capable of delivering a volume in the range from 25 to 150 μl, preferably in the range from 50 to 100 μl.

Each filled canister is conveniently fitted into a suitable channeling device prior to use to form a metered dose inhaler for administration of the medicament into the lungs of a patient. Suitable channeling devices comprise, for example a valve actuator and a cylindrical or cone-like passage through which medicament may be delivered from the filled canister via the metering valve to the mouth of a patient e.g. a mouthpiece actuator.

In a typical arrangement the valve stem is seated in a valve stem receptacle into the nozzle block which has an orifice leading to an expansion chamber. The expansion chamber has an exit orifice which extends into the mouthpiece. Actuator exit orifices having a diameter in the range from 0.10 to 0.45 mm and a length from 0.30 to 1.7 mm are generally suitable.

In a preferred embodiment of the invention, it may be useful to utilize actuator orifices having a diameter ranging from 0.12 to 0.30 mm. The use of said fine orifices may also increase the duration of the cloud generation and hence, may facilitate the coordination of the cloud generation with the slow inspiration of the patient.

Optionally the pMDI device having stainless steel can containing the formulation of the invention may be utilized together with suitable auxiliary devices favouring the correct use of the inhaler. Said auxiliary devices are commercially available and, depending on their shape and size, are known as "spacers", "reservoirs" or "expansion chambers". In addition, the formulation of the invention may be administered through an actuator provided with a mechanical or electronic dose counter or dose indicator known in the art. Such a dose counter or dose indicator may show, respectively, the number or the range of the doses administered and/or the number or the range of the doses still remaining into the can.

According to a further aspect of the invention there is provided a method of filling an aerosol inhaler with a formulation of the invention. Conventional bulk manufacturing methods and machinery well known in the art of pharmaceutical aerosol manufacture may be employed for the preparation of large-scale batches for the commercial production of filled canisters.

The packaged formulation of the invention is stable for extended periods of time when stored under normal conditions of temperature and humidity. In a preferred embodiment the packaged formulation is stable for over 3 months at 25° C. and 60% RH, more preferably for at least 6 months. Stability is assessed by measuring content of residual active ingredient and content of impurities/degradation products. A "stable" formulation as defined herein means that the content of residual active ingredient is of at least about 90% w/w (which is the content percent by weight with respect to its initial content at time 0), preferably of at least about 95% w/w, and that the total content of degradation product is of not more than about 10% by weight with respect to initial content of the active ingredient at time 0, preferably of not more than about 5% by weight, at a given time point, as measured by HPLC/UV-VIS.

The optimized stable formulations meet the specifications required by the ICH Guideline Q1A(R2) relevant for drug product stability testing for the purposes of drug registration.

Example 1

Stability of a Triple Combination Aerosol Solution Formulation Stored at 25° C. and 60% Relative Humidity (RH)

A study was performed to investigate the stability of a triple combination of formoterol fumarate (FF), glycopyrronium bromide (GLY) and beclometasone dipropionate (BDP) in an aerosol solution formulation as shown in Table 1 and which was stored for 3 months at 25° C. and 60% relative humidity (RH), in different kinds of can, crimped with different kinds of valve.

TABLE 1

Components of the aerosol solution formulation of the triple combination of formoterol fumarate (FF) dihydrate, glycopyrronium bromide (GLY) and beclometasone dipropionate (BDP). Content % w/w means the percent content by weight of each component, with respect to the total weight of the composition.

| Component | Mass in µg per actuation (63 µL) | Mass in µg/µL | Content % (w/w) |
|---|---|---|---|
| BDP | 100 | 1.59 | 0.135 |
| FF dihydrate | 6 | 0.095 | 0.0081 |
| GLY | 12.5 | 0.20 | 0.0169 |
| Ethanol (anhydrous) | 8856 | 140.57 | 12.000 |
| 1M HCl | 14 | 0.22 | 0.0019 |
| HFA 134a | 64811.52 | 1028.75 | 87.820 |

Sample batches were stored in inverted orientation, thus simulating the worst case condition for the drug product stability.

3 canisters for each batch were analysed for residual content of active ingredients and total formoterol degradation products (among which DP3: corresponding to N-(3-bromo)-[2-hydroxy-5-[1-hydroxy-2-[1-(4-methoxyphenyl) propan-2-ylamino]ethyl]phenyl]formamide) at the 3 months checkpoint.

The DP3 structure was identified by HPLC/MS/MS experiments performed on degraded samples of a triple combination of formoterol fumarate, glycopyrronium bromide and beclometasone dipropionate in an aerosol solution formulation.

To attribute the position of the substituting bromine atom, a triple combination of deuterated formoterol fumarate (N-(3-deutero)-[2-hydroxy-5-[1-hydroxy-2-[1-(4-methoxyphenyl)propan-2-ylamino]ethyl]phenyl]formamide), glycopyrronium bromide and beclometasone dipropionate was manufactured in plain aluminium cans, crimped with valves provided with EPDM (ethylene propylene diene monomer) rubber seals (RB700 from Bespak) and stored at 40° C. and 75% RH for 1 month. The analysis of the degradation products pointed out that the deuterium atom of deuterated formoterol fumarate was substituted by the bromine atom giving the degradation product DP3. Moreover N-(3-bromo)-[2-hydroxy-5-[1-hydroxy-2-[1-(4-methoxyphenyl) propan-2-ylamino]ethyl]phenyl]formamide standard was synthesized and characterized by $^1$H-NMR and MS/MS analysis. MS/MS spectrum of N-(3-bromo)-[2-hydroxy-5-[1-hydroxy-2-[1-(4-methoxyphenyl) propan-2-ylamino] ethyl]phenyl]formamide standard showed a fragmentation pattern comparable to the fragmentation pattern of DP3.

The residual content of each active ingredient, DP3 and the total amount of formoterol degradation products were measured using a validated HPLC/UV-VIS method. A mass spectra detector was used to confirm the molecular weights of the detected degradation products found in each can.

The results, summarised in the following Table 2 showed that, after 3 months at 25° C./60% relative humidity (RH), the configurations performing the best results in term of higher active ingredient content (in particular of glycopyrronium bromide and formoterol), the lowest levels of total formoterol degradation products (with respect to the theoretical formoterol fumarate content of 6 µg/actuation) and, unexpectedly, in degradation product DP3 lower than the limit of quantification of 0.10% w/w (with respect to theoretical formoterol fumarate content of 6 µg/actuation), were those wherein the formulation was stored in cans made in stainless steel according to the present invention.

As it can be appreciated, the formulation of the invention packaged in stainless steel cans showed degradation product DP3 even level lower than the limit of quantification of 0.10% w/w (with respect to the initial formoterol fumarate content), total formoterol degradation product levels lower than 2% w/w (with respect to the initial formoterol fumarate content) and the maintenance of formoterol fumarate, the most instable component of the composition, residual level higher than 95% w/w after storage in the present conditions.

TABLE 2 results of the stability test performed on the formulation stored for 3 months at 25° C. and 60% relative humidity (RH)

| CAN | VALVE | CRIMPING | FF RESIDUAL (% w/w vs time 0) | GLY RESIDUAL (% w/w vs time 0) | BDP RESIDUAL (% w/w vs time 0) | DP3 (% w/w vs FF content) | TOTAL AMOUNT OF FORMOTEROL DEGRADATION PRODUCTS (% w/w vs FF content) |
|---|---|---|---|---|---|---|---|
| Stainless steel 1 | EPDM 3 | Normal | 95.3 | 97.3 | 97.8 | <0.10 | 0.9 |
| Stainless steel 1 | EPDM 4 | Normal | 95.1 | 97.5 | 99.0 | <0.10 | 1.0 |
| Stainless steel 1 | EPDM 4 | Normal | 93.8 | 98.2 | 98.4 | <0.10 | 1.0 |
| Anodised aluminium | EPDM 4 | Normal | 90.7 | 97.5 | 98.6 | 0.4 | 2.6 |
| Anodised aluminium | EPDM 5 | Normal | 88.5 | 97.3 | 101.1 | 1.6 | 4.9 |
| Plasma coated aluminium | EPDM 5 | Normal | 94.0 | 99.0 | 98.7 | 1.2 | 2.2 |
| Fluorine passivated aluminium surface | EPDM 5 | Normal | 95.2 | 99.2 | 99.6 | 0.9 | 2.6 |
| Stainless steel 2 | EPDM 2 | Normal | 92.0 | 98.7 | 97.9 | <0.10 | 1.29 |
| Stainless steel 2 | EPDM 3 | Normal | 94.3 | 98.7 | 97.5 | <0.10 | 1.03 |

TABLE 2-continued results of the stability test performed on the formulation stored for 3 months at 25° C. and 60% relative humidity (RH)

| CAN | VALVE | CRIMPING | FF RESIDUAL (% w/w vs time 0) | GLY RESIDUAL (% w/w vs time 0) | BDP RESIDUAL (% w/w vs time 0) | DP3 (% w/w vs FF content) | TOTAL AMOUNT OF FORMOTEROL DEGRADATION PRODUCTS (% w/w vs FF content) |
|---|---|---|---|---|---|---|---|
| Stainless steel 2 | EPDM 4 | Normal | 93.8 | 98.2 | 98.4 | <0.10 | 1.03 |
| Stainless steel 2 | EPDM 6 | Normal | 91.7 | 97.7 | 95.5 | <0.10 | 1.13 |

Different numbers near each valve or can definitions define different kinds of can or valve from same or different suppliers as reported: Valves: EPDM 2 and 3 represent respectively Bespak: BK700, BK701; EPDM 4 to 6 represent respectively Aptar 808, 810 and 820; Cans: Stainless Steel 1 represents stainless steel 904L from Pressteck; Stainless Steel 2 represents stainless steel 316L from Presspart; Anodised aluminium, plasma coated aluminium and fluorine passivated aluminium surface cans were from Presspart.

The invention claimed is:

1. A pharmaceutical aerosol solution formulation contained in an aerosol can made of stainless steel, wherein the solution formulation comprises:
 (a) glycopyrronium bromide at a dosage in the range of from 5 to 26 μg per actuation;
 (b) formoterol, or a salt or a solvate thereof, at a dosage in the range of from 1 to 25 μg per actuation;
 (c) a HFA propellant;
 (d) a co-solvent;
 (e) a mineral acid; and optionally
 (f) an inhalation corticosteroid;
 wherein the stainless steel is selected from grade 904L, 316, 316L, 305, 304, 304L, 6Mo, or 2205.

2. The pharmaceutical aerosol solution formulation according to claim 1, wherein said glycopyrronium bromide is present in an amount from 6 to 25 μg per actuation.

3. The pharmaceutical aerosol solution formulation according to claim 1, wherein said formoterol, or a salt or a solvate thereof is present in an amount from 6 to 12 μg per actuation.

4. The pharmaceutical aerosol solution formulation according to claim 1 wherein the HFA propellant is HFA134a, HFA 227, HFA152a or a mixture thereof.

5. The pharmaceutical aerosol solution formulation according to claim 1, wherein the co-solvent is a (C1-C4) alkyl alcohol.

6. The pharmaceutical aerosol solution formulation according to claim 5, wherein the co-solvent is ethanol in a concentration suitable to completely dissolve the active ingredients in the formulation.

7. The pharmaceutical aerosol solution formulation according to claim 6, wherein ethanol is anhydrous ethanol at a concentration comprised from 5 to 30% w/w on the total weight of the formulation.

8. The pharmaceutical aerosol solution formulation according to claim 1, wherein the mineral acid is a pharmaceutically acceptable monoprotic or polyprotic acid.

9. The pharmaceutical aerosol solution formulation according to claim 8, wherein the mineral acid is hydrochloric acid.

10. The pharmaceutical aerosol solution formulation according to claim 9, wherein the mineral acid is 1M hydrochloric acid in an amount in the range from 0.1 to 0.3 μg/μl of the formulation.

11. A pharmaceutical aerosol solution formulation according to claim 1, characterised in that the amount of the degradation product N-(3-bromo)-[2-hydroxy-5-[1-hydroxy-2-[1-(4-methoxyphenyl) propan-2-ylamino]ethyl] phenyl]formamide is lower than 0.10% w/w with respect to the theoretical formoterol fumarate content of 6 μg/actuation when stored in accelerated conditions at 25° C. and 60% relative humidity (RH) for at least 3 months.

12. A pharmaceutical aerosol solution formulation according to claim 1, wherein the formoterol salt is formoterol fumarate.

13. A pharmaceutical aerosol solution formulation according to claim 1, wherein the solvate form of the formoterol salt is formoterol fumarate dihydrate.

14. A pharmaceutical aerosol solution formulation according to claim 1, wherein the inhalation corticosteroid is selected from the group of beclometasone dipropionate, budesonide or its 22R-epimer, ciclesonide, flunisolide, fluticasone propionate, fluticasone furoate, mometasone furoate, butixocort, triamcinolone acetonide, triamcinolone, methylprednisolone, prednisone, loteprednol and rofleponide.

15. A pharmaceutical aerosol solution formulation according to claim 14 wherein the inhalation corticosteroid is beclometasone dipropionate.

16. A pharmaceutical aerosol solution formulation according to claim 15, wherein the beclometasone dipropionate is present in an amount in the range from 50 to 250 μg per actuation.

17. A pharmaceutical aerosol solution formulation according to claim 16, wherein the beclometasone dipropionate is present in the amount of 100 or 200 μg per actuation.

18. A pharmaceutical aerosol solution formulation according to claim 1, wherein the overall formoterol degradation products level is lower than 10% w/w with respect to the theoretical formoterol fumarate content of 6 μg/actuation and the residual level of formoterol fumarate is higher than 90% w/w with respect to its initial content.

19. A pharmaceutical aerosol solution formulation according to claim 1, wherein the overall formoterol degradation products level is lower than 2% w/w with respect to the theoretical formoterol fumarate content of 6 μg/actuation and the residual level of the formoterol fumarate is higher than 95% w/w with respect to its initial content.

20. An aerosol can made of stainless steel selected from grade 904L, 316, 316L, 305, 304, 304L, 6Mo, or 2205 containing a pharmaceutical aerosol solution formulation according to claim 1, suitable for use in a pressurised metered dose inhaler.

21. A pressurised metered dose inhaler comprising a can according to claim 20.

22. A method to lower the amount of degradation product N-(3-bromo)-[2-hydroxy-5-[1-hydroxy-2-[1-(4-methoxyphenyl) propan-2-ylamino]ethyl]phenyl]formamide (DP3) during the shelf-life of a pharmaceutical aerosol solution formulation according to claim 1, said method being characterised in containing said aerosol solution formulation in an aerosol can made of stainless steel.

23. The pharmaceutical aerosol solution formulation according to claim 1, wherein the stainless steel is selected from grade 904L, 316, or 316L.

* * * * *